United States Patent [19]

Dolby

[11] 4,259,512

[45] Mar. 31, 1981

[54] METHOD OF SYNTHESIS FOR A CHEMICAL PRECURSOR TO STRIGOL

[75] Inventor: Lloyd J. Dolby, Eugene, Oreg.

[73] Assignee: State Board of Higher Education for and on Behalf of the University of Oregon

[21] Appl. No.: 732,722

[22] Filed: Oct. 15, 1976

[51] Int. Cl.$^3$ ............................................. C07L 67/333
[52] U.S. Cl. .................................... 560/119; 560/126; 562/501; 562/508
[58] Field of Search ...................... 260/468 G, 514 G; 560/119, 126; 562/501, 508

[56] References Cited

PUBLICATIONS

Dolby et al., J.O.C. 41 563 (1976).
House, Modern Synthetic Reactions, pp. 606–611, 740–741, (1972).

*Primary Examiner*—Robert Gersil
*Attorney, Agent, or Firm*—Kolisch, Hartwell & Dickinson

[57] ABSTRACT

Preparation of 5,5-Dimethyl-8-carboalkoxybicyclo [4.3.0]non-1-(6)-ene-2,7-dione by condensing dimethylpyruvic acid and 5-ono-6-heptenoic acid to produce a dibasic acid. Esterification of the acid produces a diester which is cyclized to produce the compound.

4 Claims, No Drawings

METHOD OF SYNTHESIS FOR A CHEMICAL PRECURSOR TO STRIGOL

This invention relates to the preparation of a beta-keto ester having utility as a precursor or intermediate in the synthesizing of strigol, analogs of strigol, and other strigol related compounds.

Strigol is a potent seed germination stimulant for the root parasite witchweed (*Striga lutea* Lour). The compound has been isolated from the root exudates of cotton, but it was not until relatively recently that the structure of the compound was reported (C. E. Cook et al, J. Am. Chem. Soc., 94, 6198 (1972)). Several synthesis of strigol differing only in the construction of the hydrindan portion of strigol have been reported (J. B. Heather et al, J. Am. Chem. Soc., 96, 1976 (1974); G. A. MacAlpine et al, J. Chem. Soc., Chem. Commun., 834 (1974)). An optimum hydrindan precursor for strigol is the beta-keto ester having the following formula

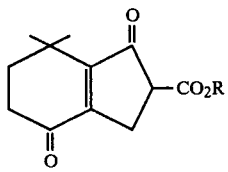

The beta-keto ester set forth above, for instance, is a key intermediate in the synthesis of strigol disclosed and described in U.S. Pat. No. 3,887,547.

The preparation of strigol disclosed in said patent relies upon the methylation of 3-oxo-2,6,6-trimethylcyclohex-1-en-1-carboxylic acid, bromination of the ester obtained, and subsequent cyclization of the brominated product producing a mixture of beta-keto ester and an enol. The production of strigol requires the separation of the beta-keto ester, which is then further processed.

Production of the beta-keto ester in the manner described has a number of deficiencies. For one thing, the production of the carboxylic acid which is the starting material is a complicated procedure which, as such is performed at this time, requires a number of manipulative steps performed on citrol, an extract obtained from lemon grass oil. In producing the carboxylic acid, the chemistry involved requires close control, and yields are poor. Both the preparation of the carboxylic acid, and the conversion of this material into the beta-keto ester, are expensive and time consuming, and involve procedures which can hardly be said to lend themselves to commercial production.

A general object of this invention, therefore, is to provide an improved method of producing a hydrindan beta-keto ester having utility, for instance, as a precursor or intermediate in the production of strigol or strigol-related compounds, which is relatively simply performed with the obtaining of good yields.

Another object is the provision of a method for making such a material which is performable using relatively readily available starting materials.

The process contemplated by the invention may be performed in far less time and with much less criticality involved than processes known to date. Good yields are obtained, and as a consequence the process contemplated constitutes a commercially feasible procedure for producing the beta-keto ester in meaningful quantities.

These and other objects and advantages of the invention will become apparent as the same is described below in conjunction with an example which specifically illustrates the invention. In the description that follows, identical compounds are identified by like numbers found in the schematic representation of a compound and in the description itself.

A beta-keto ester which may be prepared as contemplated by the invention, is 5,5-Dimethyl-8-carboalkoxybicyclo[4.3.0]non-1(6)-ene-2,7-dione (1), and such may be represented schematically by the following diagram:

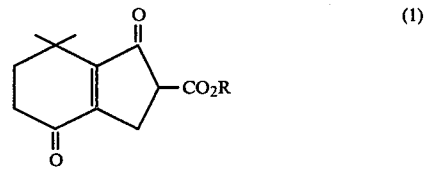

Beta-keto ester (1) is a hydrindan and may be utilized to provide the hydrindan portion of strigol and strigol-related compounds utilizing procedures as reported in the art. For instance, beta-keto ester (1) may be employed to produce dl-Strigol using the procedure set forth in U.S. Pat. No. 3,887,547.

According to the invention, two known compounds, namely dimethylpyruvic acid (2) and 5-oxo-6-heptenoic acid (3) are condensed to produce dibasic acid (4). This condensation reaction may be represented by the following equation:

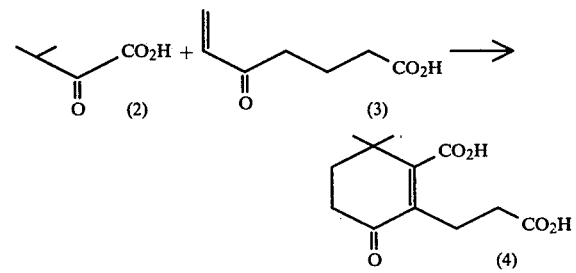

The condensation product, i.e. dibasic acid (4) is then esterified to produce diester (5) according to the following (wherein R represents an alkyl group):

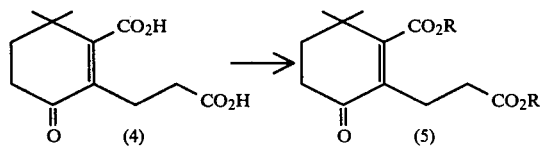

Cyclization of the diester (5) may then be performed to produce beta-keto ester (1) as set forth in the following equation:

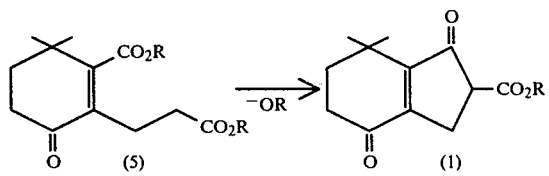

Using the procedure, the dimethylpyruvic acid (2) and 5-oxo-6-heptenoic acid (3) are condensed in an aqueous base. Good yields (70–80%) of the dibasic acid (4) are obtained. Esterification of the dibasic acid (4) may be performed to produce a quantitative yield of diester (5). The diester (5) may be cyclized to produce a nearly quantitative yield (in excess of 95%) of the keto ester (1).

Dimethylpyruvic acid (2) may be conveniently prepared by an azlactone synthesis as described by G. R. Ramage et al J. Chem. Soc., 532 (1935). The 5-oxo-6-heptenoic acid (3) may be prepared in modest yield by acylating ethylene with glutaric anhydride and aluminum chloride, although the acid and its esters have been prepared by other roots (S. Umezawa, Japanese Pat. No. 1713 (1962); Chem Abstr., 58, 7833a (1963); G. P. Vig et al, J. Indian Chem. Soc., 49, 163 (1972); L. B. Barkley et al, J. Am. Chem. Soc., 78, 4111 (1956); N. Nazarov et al, J. Gen. Chem. USSR (Engl. Transl.), 23, 1703 (1953)). The crude material from the Friedel-Crafts acylation is quite satisfactory for the condensation with dimethylpyruvic acid.

Preparation of 5-oxo-6-heptenoic Acid (3)

A mixture of aluminum chloride (66.7 g, 0.5 mol), glutaric anhydride (28.5 g, 0.25 mol), and methylene chloride (1 l.) was placed in a 2-l. three-necked flask equipped with a gas inlet tube, a drying tube, and a mechanical stirrer. Ethylene (44 g, 1.57 mol) was bubbled in during 4.5 hr with vigorous stirring, after which the reaction mixture was poured over a mixture of 5% hydrochloric acid (900 ml) and ice. The organic layer was separated and the aqueous portion was extracted once with ether (300 ml). The organic extracts were separately washed with water and evaporated under reduced pressure. The combined residues were warmed on the steam bath for 10 min with 100 ml of 10% potassium carbonate solution which resulted in a bright yellow suspension. This mixture was washed with ether until a colorless ether extract was obtained. The aqueous portion was acidified with hydrochloric acid and extracted with ether. The dried ($Na_2SO_4$) ether solution was evaporated to leave an orange oil (5.2 g, 14%) which crystallized on storage. A similar run gave a 34% yield of material with satisfactory spectroscopic properties. The material was triturated with carbon tetrachloride and collected. A sample of the crystalline material was purified by short-path distillation to produce a clear oil which gave crystalline material, mp 44°–46°, after exposure to air (lit. mp of the hydrate 45°–46.5°): ir $\nu_{max}$ ($CHCl_3$) 1710, 1685, 1618 cm$^{-1}$; $^1$H NMR 1.97 (p, 2H, J=7 Hz), 2.44 (t, 2H, J=7 Hz), 2.70 (t, 2H, J=7 Hz), 5.8–6.6 ppm (m, 3H).

Preparation of dibasic acid (4)

A solution of dimethylpyruvic acid (1.23 g, 0.0106 mol) and 5-oxo-6-heptenoic acid (1.509 g, 0.0106 mol) in 31.5 ml of 1.5 N aqueous potassium hydroxide was heated on the steam bath for 2 hr. The cooled solution was acidified with concentrated hydrochloric acid and the crystalline material (1.68 g) was collected by filtration. The $^1$H NMR spectrum of this material was identical with that of the purified substance. The filtrate was extracted with ether to afford an additional 0.411 g of crude dibasic acid 2 which was contaminated with ca. 50% by weight of dimethylpurific acid as judged by its $^1$H NMR spectrum. The total yield of crude dibasic acid 2 (2.0 g) was 79%. The crude material was recrystallized from water to yield needles, mp 205°–206.5°, with slight previous softening. Impure dibasic acid is more conveniently recrystallized from ethyl acetate. The purified material showed $^1$H NMR ($Me_2SO$-$d_6$-$CDCl_3$) 1.26 (s, 6H), 1.95 (q, 2H, J=6 Hz), 2.2–2.7 ppm (m, 6H); ir $\nu_{max}$ (KBr) 1710, 1635 cm$^{-1}$; mass spectrum m/e calcd for $C_{12}H_{16}O_5$, 240.100; found, 240.100.

Esterification of dibasic acid (4) to produce diester (5)

A sample of dibasic acid (4) in tetrahydrofuran was treated with excess ethereal diazomethane. The solvent was evaporated and the residue was sublimed to give a quantitative yield of 3: mp 47°–49°; $^1$H NMR 1.23 (s, 6H), 1.90 (t, 2H, J=7 Hz), 2.40–2.7 (m, 6H), 3.65 ppm (s, 3H); ir $\nu_{max}$ ($CHCl_3$) 1730, 1675, 1619 cm$^{-1}$; uv $\lambda_{max}$ (EtOH) 237 nm ($\epsilon$ 12360); mass spectrum m/e calcd for $C_{14}H_{20}O_5$, 268.131; found, 268.129.

Cyclization of diester (5) to produce beta-keto ester (1)

The diester (5) (0.20 g) was heated under reflux for 2 hr in a nitrogen atmosphere with 2 ml of 0.78 N sodium methoxide in methanol. The cooled solution was treated with 0.1 g of acetic acid and diluted with 1% hydrochloric acid. The crystalline material was collected by filtration and the aqueous portion was extracted with ether. The combined product was dried to give 0.173 g (98%) of 1. A sample was crystallized from methanol and sublimed to give an analytical sample, mp 136.8°–141°. The material is clearly a mixture of tautomers (ca. 1:1) in chloroform solution as previously indicated: $^1$H NMR ($CDCl_3$) 1.32, 1.38 (s, 6H), 1.96 m, 4H), 2.67 (q, 2H, J=7 Hz), 2.92 (m, 1H), 3.28 (s, 1H), 3.49 (m, 1H), 3.78, 3.83 ppm (s, 3H); ir $\nu_{max}$ ($CHCl_3$) 1740, 1715, 1680 sh, 1615, 1548 cm$^{-1}$; uv $\lambda_{max}$ (EtOH) 222 nm ($\epsilon$ 9170), 256 (7590), 325 (6478); mass spectrum m/e calcd for $C_{13}H_{16}O_4$, 236.105; found, 236.103.

Infrared spectra were measured with either Beckman IR-5A or IR-7 infrared spectrophotomers. Proton magnetic resonance spectra were determined at 100 MHz with a Varian Model XL-100 spectrometer. The chemical shift values are expressed in $\delta$ values (parts per million) relative to tetramethylsilane internal standard. In the presentation of the $^1$H NMR spectra the following notations are used: s=singlet, d=doublet, t=triplet, q=quartet, p=pentuplet, and m=multiplet.

What is claimed is:

1. A process for preparing the beta-keto ester having the formula

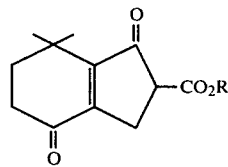

where R is an alkyl group, which comprises
condensing dimethylpyruvic acid and 5-oxo-6-heptenoic acid in an aqueous base to produce a dibasic acid condensation product, having the formula

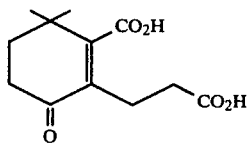

esterifying said condensation product, and cyclizing the esterified condensation product to produce the beta-keto ester.

2. The process of claim 1, wherein the esterification of the condensation product is performed by esterifying with ethereal diazomethane to produce a dimethyl ester.

3. The process of claim 1, wherein cyclizing of the esterified condensation product is performed by reacting the esterified condensation product with sodium methoxide in an alcohol.

4. A process for preparing the beta-keto ester having the formula

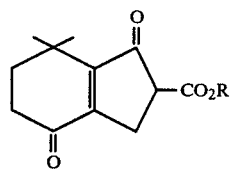

wherein R is an alkyl group, which comprises condensing dimethylpyruvic acid and 5-oxo-6-heptenoic acid to yield a compound having the formula

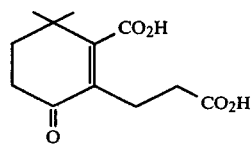

esterifying said compound to yield another compound having the formula

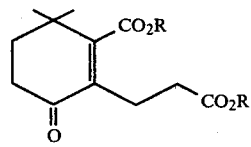

and cyclizing said other compound to produce the beta-keto ester.

* * * * *